(12) United States Patent
Gutman et al.

(10) Patent No.: US 8,382,686 B2
(45) Date of Patent: Feb. 26, 2013

(54) APPARATUS AND METHOD FOR RECORDING MANDIBULAR MOVEMENT

(75) Inventors: Yevsey Gutman, Minneapolis, MN (US); John Joseph Keller, Anoka, MN (US)

(73) Assignee: Gnath Tech Dental Systems, LLC, Anoka, MN (US)

( * ) Notice: Subject to any disclaimer, the term of this patent is extended or adjusted under 35 U.S.C. 154(b) by 690 days.

(21) Appl. No.: 12/105,246

(22) Filed: Apr. 17, 2008

(65) Prior Publication Data

US 2008/0261168 A1    Oct. 23, 2008

Related U.S. Application Data

(60) Provisional application No. 60/912,316, filed on Apr. 17, 2007, provisional application No. 60/912,278, filed on Apr. 17, 2007.

(51) Int. Cl.
*A61B 5/103* (2006.01)
*A61B 5/117* (2006.01)
*A61C 11/00* (2006.01)
*A61C 19/00* (2006.01)
*G09B 23/28* (2006.01)

(52) U.S. Cl. .......... 600/595; 600/587; 600/590; 433/57; 433/58; 433/59; 433/60; 433/61; 433/62; 433/63; 433/64; 433/65; 433/66; 433/67; 434/264

(58) Field of Classification Search .................. 600/595, 600/587, 590; 433/57–69
See application file for complete search history.

(56) References Cited

U.S. PATENT DOCUMENTS

| | | | |
|---|---|---|---|
| 2,701,915 A | 2/1955 | Page |
| 2,713,721 A | 7/1955 | Page |
| 2,772,477 A | 12/1956 | Miller |
| 2,794,253 A | 6/1957 | Fitzsimmons |
| 2,959,857 A | 11/1960 | Stoll |
| 3,052,030 A | 9/1962 | Spence |
| 3,084,438 A | 4/1963 | Goodfriend |
| 3,200,497 A | 8/1965 | Goodfriend |
| 3,218,716 A | 11/1965 | Stuart |
| 3,431,649 A | 3/1969 | Guichet |

(Continued)

FOREIGN PATENT DOCUMENTS

| DE | 4112080 A1 | 10/1992 |
|---|---|---|
| EP | 0 170 806 | 5/1985 |

(Continued)

OTHER PUBLICATIONS

Treil, Jacques et al., "Three Dimensional Cephalometry", Alpha Omegan, Dec. 2001, pp. 34-39, vol. 94, No. 4.

(Continued)

*Primary Examiner* — Sean P Dougherty
*Assistant Examiner* — Devin Henson
(74) *Attorney, Agent, or Firm* — DuFault Law Firm, P.C.; Dustin R. DuFault

(57) ABSTRACT

An apparatus for use in dentistry to obtain positional data related to movement of a mandible about a maxilla comprises a rigid support frame for supporting a maxilla support member, a positionable mandibular member and sensing assemblies. The support member fixedly attaches to the support frame. The mandibular member is positionable proximate the maxilla member. The sensing assemblies attach to the support frame and connect to the mandibular member to obtain positional data related to the movement of the mandibular member. The positional data is collected by a computing device and stored in a data storage medium as time history files. The files can then be transformed into usable information to replicate the mandibular movement in real time either virtually or mechanically.

17 Claims, 12 Drawing Sheets

U.S. PATENT DOCUMENTS

| | | | | |
|---|---|---|---|---|
| 3,577,639 A | | 5/1971 | Lee | |
| 3,908,271 A | * | 9/1975 | Derda et al. | 433/58 |
| 4,014,097 A | * | 3/1977 | Pameijer | 433/27 |
| 4,026,024 A | | 5/1977 | Tradowsky | |
| 4,034,475 A | | 7/1977 | Lee | |
| 4,204,326 A | | 5/1980 | Dimeff | |
| 4,292,026 A | * | 9/1981 | Yokota | 433/69 |
| 4,354,836 A | | 10/1982 | Santoni | |
| 4,386,405 A | | 5/1983 | Lewin et al. | |
| 4,447,207 A | | 5/1984 | Kataoka et al. | |
| 4,468,198 A | | 8/1984 | Kataoka et al. | |
| 4,537,574 A | | 8/1985 | Clark | |
| 4,561,846 A | * | 12/1985 | Polizzotto | 433/73 |
| 4,587,977 A | | 5/1986 | Meyer et al. | |
| 4,611,288 A | | 9/1986 | Duret et al. | |
| 4,639,220 A | | 1/1987 | Nara et al. | |
| 4,668,189 A | | 5/1987 | Levandoski | |
| 4,673,352 A | | 6/1987 | Hansen | |
| 4,681,539 A | | 7/1987 | Knap | |
| 4,773,854 A | | 9/1988 | Weber | |
| 4,788,987 A | * | 12/1988 | Nickel | 600/590 |
| 4,859,181 A | | 8/1989 | Neumeyer | |
| 4,955,367 A | | 9/1990 | Homsy | |
| 5,006,065 A | * | 4/1991 | Waysenson | 433/63 |
| 5,020,993 A | | 6/1991 | Levandoski | |
| 5,076,786 A | | 12/1991 | Callne | |
| 5,131,844 A | | 7/1992 | Marinaccio et al. | |
| 5,160,262 A | | 11/1992 | Alpern et al. | |
| 5,257,932 A | | 11/1993 | Leinfelder et al. | |
| 5,273,429 A | | 12/1993 | Rekow et al. | |
| 5,320,528 A | | 6/1994 | Alpern et al. | |
| 5,338,198 A | | 8/1994 | Wu et al. | |
| 5,340,309 A | | 8/1994 | Robertson | |
| 5,372,502 A | | 12/1994 | Massen et al. | |
| 5,380,199 A | | 1/1995 | Koutavas | |
| 5,595,485 A | | 1/1997 | Shepard | |
| 5,738,515 A | | 4/1998 | Leever | |
| 6,024,563 A | | 2/2000 | Shiraishi et al. | |
| 6,106,285 A | | 8/2000 | Kwak | |
| 6,120,290 A | | 9/2000 | Fukushima et al. | |
| 6,152,731 A | | 11/2000 | Jordan et al. | |
| 6,223,648 B1 | | 5/2001 | Erickson | |
| 6,322,359 B1 | | 11/2001 | Jordan et al. | |
| 6,551,102 B1 | | 4/2003 | Morales et al. | |
| 6,564,464 B1 | | 5/2003 | Keating et al. | |
| 7,182,737 B2 | | 2/2007 | Kim et al. | |
| 7,347,690 B2 | | 3/2008 | Jordan et al. | |
| 1,033,562 A1 | | 7/2012 | Eltner | |
| 2006/0072799 A1 | | 4/2006 | McLain | |

FOREIGN PATENT DOCUMENTS

| | | |
|---|---|---|
| JP | 402001241 A | 1/1990 |
| JP | 02000107207 A | 4/2000 |
| JP | 02001112743 A | 4/2001 |

OTHER PUBLICATIONS

Muecke, S.R., "Clinical Significance of Dental AART Technology: Three-Dimensional, Volumetric, Anatomically Accurate Individual Patient Capture", Alpha Omegan, Dec. 2001, pp. 57-63, vol. 94, No. 4.

Supplemental European Search Report, European App. No. EP 08 74 6162, Mar. 14, 2012.

\* cited by examiner

APPARATUS AND METHOD FOR RECORDING MANDIBULAR MOVEMENT

CROSS-REFERENCE TO RELATED APPLICATION(S)

This application claims the benefit of U.S. Provisional Patent Application No. 60/912,316 entitled APPARATUS TO MEASURE, RECORD AND ANALYZE LOWER JAW MOVEMENT IN REAL TIME AND METHODS OF USING SAME, and U.S. Provisional Patent Application No. 60/912,278 entitled APPARATUS FOR VIRTUALLY REPRESENTING JAW MOVEMENT AND METHODS OF USING SAME, each filed on 17 Apr. 2007, both of which are hereby incorporated herein by reference.

BACKGROUND OF INVENTION

The present invention generally relates to dental restorative or corrective work. In particular, the present invention relates to an apparatus for measuring, recording and analyzing mandibular movement for use in dental restorative and corrective work.

In restorative dentistry, it is critical that proper occlusion between the upper and lower jaws of a patient be established to maximize comfort of the patient during mastication. In corrective dentistry, especially that concerning those suffering from tempormandibular joint syndrome, a full and complete understanding of a specific patient's jaw movement is needed in order to properly diagnose and implement a treatment plan for the patient. Improper occlusion may not only lead to the discomfort of the patient while chewing, but may also contribute to other chronic debilitating affects, including improperly aligned condyles. Because such occlusion of the upper and lower teeth is so closely related to condylar movement about the tempormandibular joint, a complete understanding of such movement is essential in making gnathological determination factors related to the dental restorative or corrective work.

Occlusal motion is quite complex. While a dominant factor of occlusal motion includes pivotal movement of the lower jaw about a hinge axis through the TMJ, other factors contributing to the movement include torsional and linear movement of the lower jaw. Such movement can be characterized as having factors relating to pitch, yaw and roll, as well as linear movement transverse to the condylar axis. It has therefore been quite difficult to not only record mandibular movement, but also precisely replicating such movement within precise tolerances.

There exist in the art a wide variety of devices which have attempted to record mandibular movement. Perusing the prior art, incremental changes in the attempts to record such mandibular movement can be observed. Early examples include dental pantographs, such as those suggested by U.S. Pat. No. 1,033,562 and U.S. Pat. No. 2,794,253. These pantographs had several inherent shortcomings, including ease of use, discomfort when applied to the patient and overall accuracy of recording. Other examples of dental pantographs include: U.S. Pat. No. 3,218,716; U.S. Pat. Nos. 3,431,649; and 4,034,475. Briefly, using such pantographic recording systems, dentists attach mechanical devices, or clutches, to the upper jaw and the lower jaw of patient. This system of clutches allowed the dentist to attach a network of connecting bars and linkages to the upper and lower jaws of the patient. Each clutch is filled with a compound material which forms a surface around the teeth of the patient, then a cement is used to temporally attach the clutch thereto. Each clutch is in turn operatively linked to a pantograph such that the dentist can guide the jaws and record the resulting movement pattern. Using a stylus and magnetic pads to record the movements of the jaw, a set of tracings in the form of trajectories were obtained.

The resulting tracings have the appearance of a regular strip charge recorder with no interface to any data storage device for future analysis. Despite the accuracy of the aforementioned pantographic systems, the overall time required to prepare the system with the patient and the overall difficulty in using the pantographic system has hindered its widespread growth. Subsequently, less accurate but more workable systems are have become more popular.

More recently, there have been other attempts to record mandibular movement. One such attempt includes supplementing the recording surface of the aforementioned dental pantographs with pressure sensitive elements capable of transmitting an electric signal. Such devices, however, still did not accurately and precisely depict three-dimensional motion of the jaw.

Another example includes the use of corresponding arrays of ultrasonic transmitters and receivers in order to record jaw movement with at least six degrees of the freedom. This attempt again required the patient to wear the entire device in order to record movement of the lower jaw. Also, this attempt has inherent accuracy and precision issues as the contact points for the arrays within each jaw are secluded to a single area which, for example, can compound errors when determining roll characteristics of mandibular movement.

An even further example includes the use of video cameras to optically capture a target image attached to a tooth on the upper jaw and a target image attached to a tooth on the lower jaw of the patient. This attempt also has inherent accuracy and precision issues as the contact points within each jaw are secluded to movement of the lower jaw about a single tooth, which may not accurately or precisely record roll or uneven pivoting about the condyles.

BRIEF SUMMARY OF INVENTION

The present invention includes an apparatus for recording and analyzing in real time mandibular movement, or the movement of the mandible (lower jaw) of a patient relative to the maxilla (upper jaw) of the patient. The apparatus includes a recording device which is suspended by a wrist mechanism and revolute arm such that the recording device is freely positionable proximate the patient. The recording device includes three electro-mechanical sensors positioned substantially orthogonal to one another. Each sensor is designed to be positionable about three degrees of freedom to collect pitch, yaw and translational movement proximately along its respective axis. A freely moveable recording bar connects to each sensor. The maxilla of the patient is fixedly securable to the recording device, whereupon securing the mandible to the recording bar, mandibular movement in the form of positional data is obtained from each of the three sensors and stored into a computer as time history files. Dental casts of the lower and upper jaws of the patient are digitally scanned in such a manner to preserve their occlusal relationship based upon a hinge axis reference. The time history files and the digital scans of the dental casts can then be processed by the computer to replicate the mandibular movement of the patient in either a virtual environment or on an electro-mechanical articulator.

DETAILED DESCRIPTION

Figure 1:
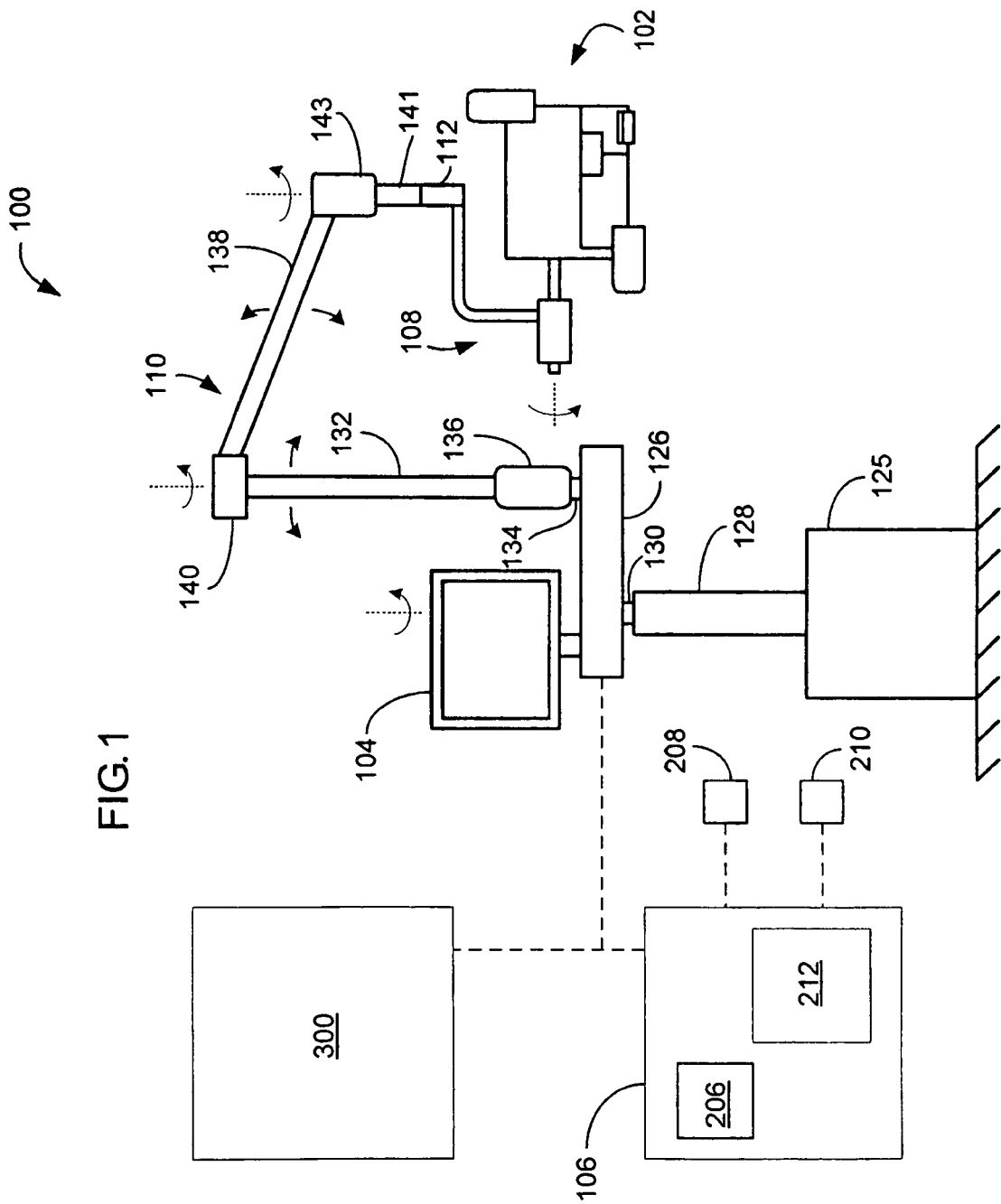
FIG. 1 is an overall view of the present invention showing a general arrangement of components.
Figure 2:
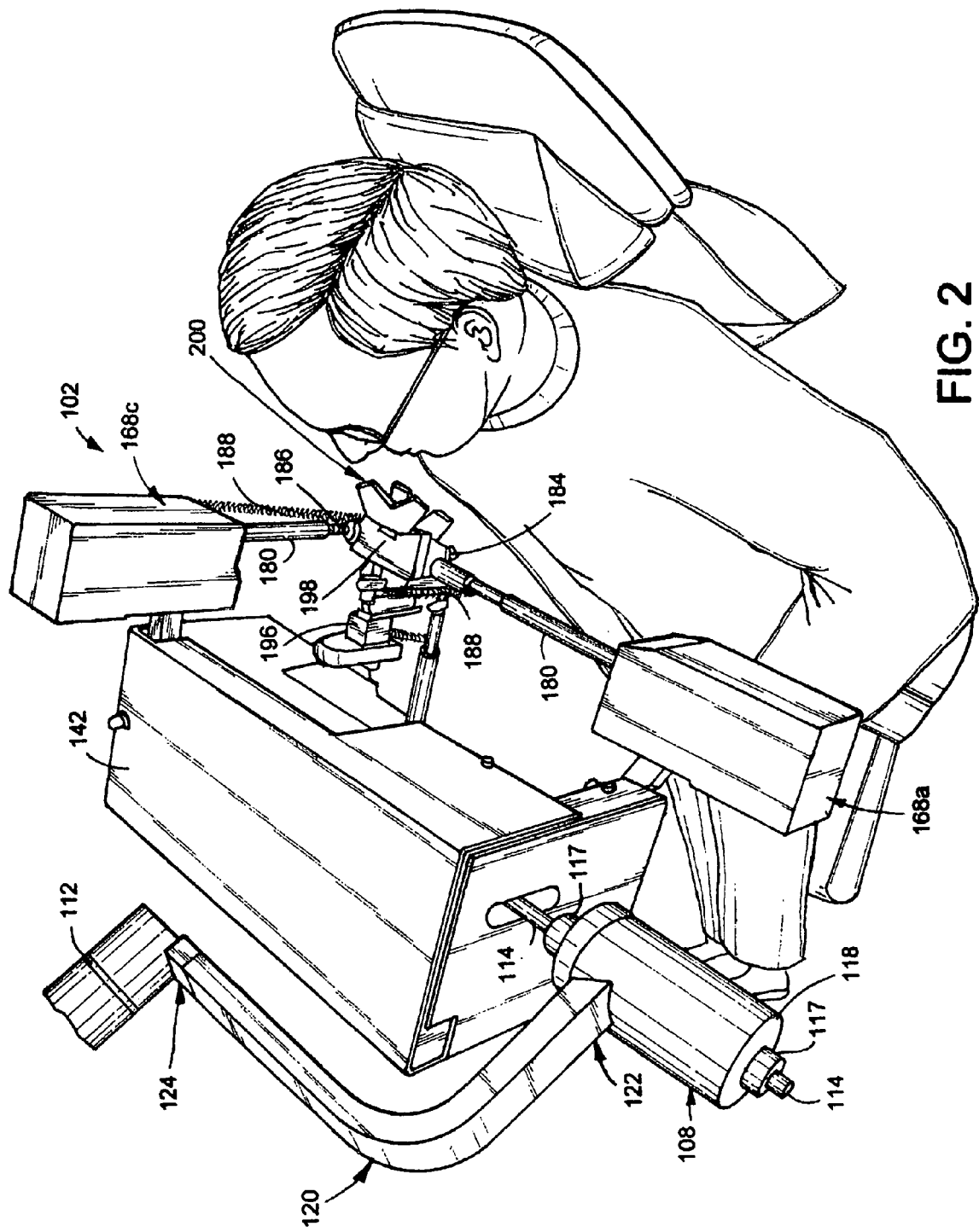
FIG. 2 is a perspective view of a recording device of the present invention positioned proximate a patient.

A dental recording system of the present invention for recording and analyzing mandibular movement in real time is generally indicated at 100 in FIG. 1. Generally, the system includes a recording apparatus 102, connected to a user interface 104 and computing means 106, and supported by a wrist device 108 and revolute arm 110. Both the wrist device 108 and revolute arm 110 allow the recording apparatus 102 to be positionable proximate a patient, as illustrated in FIG. 2, and suspend the recording apparatus 102 at any desired position.

The wrist device 108 is positionable within three degrees of freedom, providing for pitch, roll and yaw orientation of the recording apparatus 102 when attached thereto. The wrist device 108 includes a rod 114 having a distal end pivotally attached to the recording apparatus 102 by means of a rotational joint 116 allowing the recording apparatus 102 to be positioned with roll orientation. An opposing proximal end of the rod 114 disposes upon a set of bearings 117 contained within a housing 118, allowing pitch positioning of the recording apparatus 102. The wrist device 108 further includes a connecting arm 120 having a proximal end 122 fixedly attached to an outer surface of the housing 118 and a distal end 124 rotatably attached to the revolute arm 110, also by means of a rotational joint 112, allowing yaw positioning of the recording apparatus 102. Preferably, each rotational joint used in construction of the wrist 108 includes low friction bearings to reduce the effort of angularly positioning the recording apparatus 102 during both the initial setup with the patient and throughout the recording process.

To suspend and maneuver the wrist 108 and recording device 102 proximate to the patient, FIG. 1 illustrates the revolute arm 110 being secured to the ground by a base 125. A horizontal segment 126 rotationally connects to a vertical member 128 secured to the base 125 by means of a rotational joint 130. An upright segment 132 in turn connects to the horizontal segment 126 by means of a second rotational joint 134, providing rotational positioning of the upright segment 132 along a vertical axis. However, the upright segment 132 also includes a pivotal joint 136 positioned proximate the rotational joint 134, allowing the upright segment 132 to be pivoted past the vertical. Springs (not shown) positioned inside the upright segment provide balance and allow the upright segment 132 to maintain its positioning, as is known in the art. Pivotally attached to an opposing end of upright segment 132 is the segment 138. Segment 138 connects to the upright segment 132 by means of pivotal joint 140, which allows segment 138 to be pivoted relative to the upright segment 132. Finally, connection segment 141 pivotally attaches segment 138 by means of join pivotal joint 143 and joins the wrist 108 to the revolute arm by connecting to pivotal joint 112. Segments 132 and 138 each contains springs (not shown) positioned inside to maintain positioning thereof. It should be noted that although only three degrees of freedom are needed to position the arm, the revolute arm 110 has four degrees of freedom, which not only allows the wrist 108, and subsequently the recording apparatus 102, to be infinitely positionable within three-dimensional space, but the added degree of freedom provides flexibility in orientation around the vertical axis, enhancing the ease at which the wrist 108 can initially position the recording apparatus 102 relative to the patient.

It should be noted that the base 125 of the revolute arm 110 should be secured to the ground in such a manner that the recording apparatus 102 and wrist 108 can be suspended therefrom without toppling over. This may be accomplished by providing flat platform with an appropriate amount of surface area, or providing the base 125 with an appropriate amount of mass, such as by securing weights to the base 125. Alternatively, the base member 125 can be permanently affixed to the ground by bolting or otherwise cementing the base 125 to the floor. It should be noted, though, that any means necessary to secure the base 125 to the ground is well within the scope of the present invention. Upon properly securing the base 125 to the ground, both the wrist device 108 and revolute arm 110 allow the recording apparatus 102 to be both easily positionable proximate a patient and hold the recording apparatus at any desired position.

Referring again to FIG. 3, the recording device 102 is illustrated with protective shields 142 removed therefrom. The recording device 102 includes a frame 144 built as a spatial three-dimensional structure to achieve light-weight characteristics coupled with high rigidity. The frame 144 includes four longitudinal bars 146 positioned in rectangular formation and connected at each end with connecting bars 148. Centrally positioned cross bars 150 provide rigidity to the frame 144 and assist in attaching the wrist device 108 thereto by means of the rotational joint 116, as previously discussed. The frame further includes an "L"-shaped sub-structure 152 extending downwardly therefrom for attaching mounting plates 154. A first mounting plate 154a attaches to a first leg 156 of the sub-structure 152 proximate a lower forward corner 158 of the frame 144. A second mounting plate 154b attaches to a second leg 160 of the sub-structure 152 proximate a lower central rearward portion of the frame 162. A third mounting plate 154c attaches to an upper forward corner 166 of the frame 144. The mounting plates 154 are for attaching sensor assemblies 168a, 168b, 168c to the frame 144.

Figure 4:
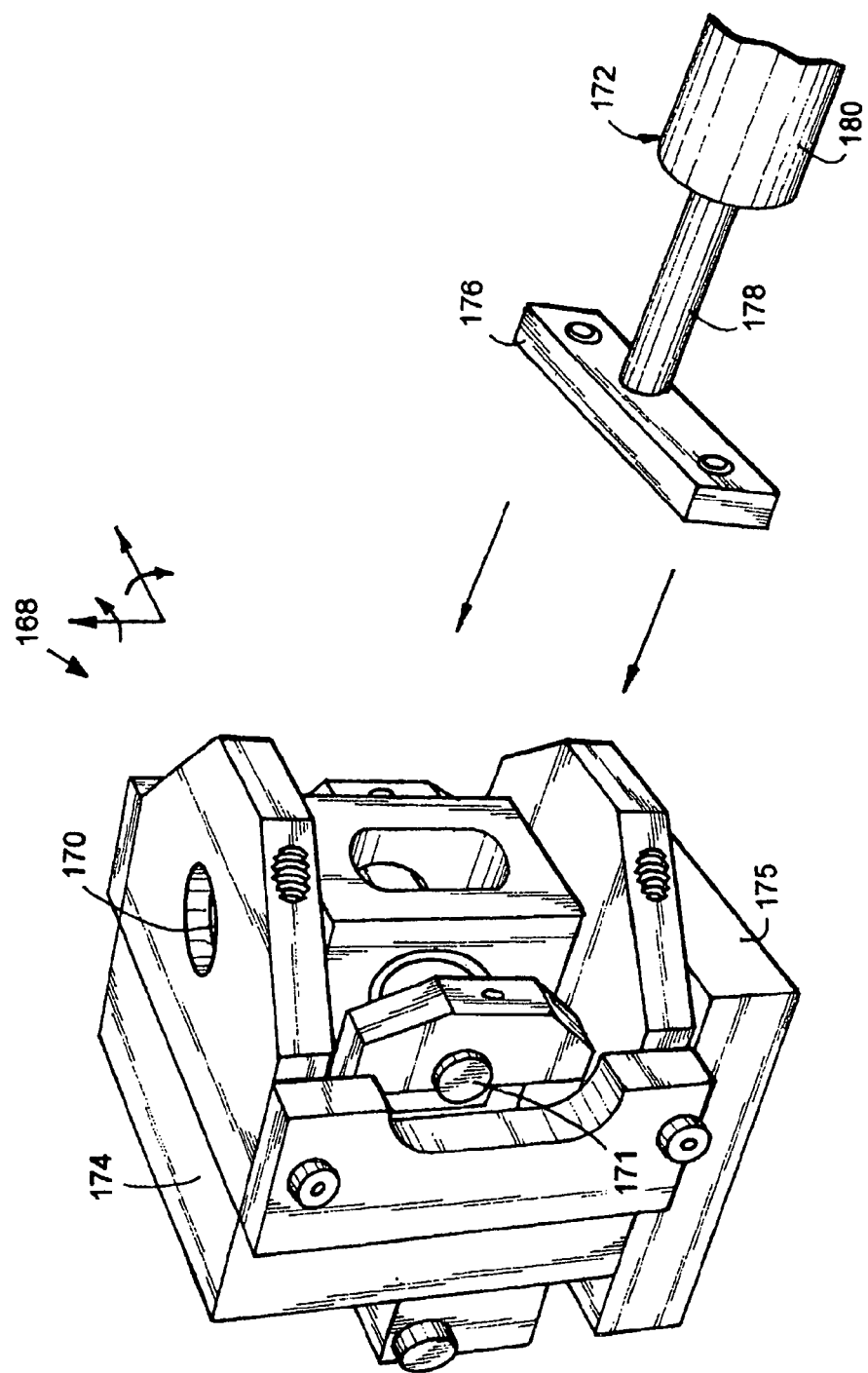
FIG. 4 is a perspective view of a sensor assembly of the present invention.

As illustrated in FIG. 4, each sensor assembly 168a, 168b, 168c includes first and second rotational joints, 170 and 171 respectively, and a linear translational joint 172. The first and second rotational joints, 170, 171 are disposed upon a housing member 174, and act like cooperating gimbals wherein the first joint 170 is pivotal relative the housing member 174 and the second joint 171 is pivotal orthogonal to the first joint 170. The housing member is attached to a base plate 175 which is attachable to the respective mounting plate 154. A crossbar 176 connects the linear translational joint 172 to the second angular joint 171. The linear joint 172 includes a sensor rod 178 disposed within a tube 180 for detecting the positioning of the tube 180 relative to the rod 178. Angular joint information is monitored by a pair of linear optical encoders, 182 and 183 respectively, mounted to the housing member 174. Each of the aforementioned sensors 182, 183 is commercially available by Heidenhain Corporation of Schaumburg, Ill. After the sensor assemblies 168a, 168b, 168c are mounted onto the frame 144, a set of calibrating fixtures (not shown) are used to verify and adjust their positioning. Proper alignment of the sensor assemblies 168a, 168b, 168c ensures squareness of the recording system 102, establishes a proper home position and zeros all sensor assemblies at this home position.

Figure 3:
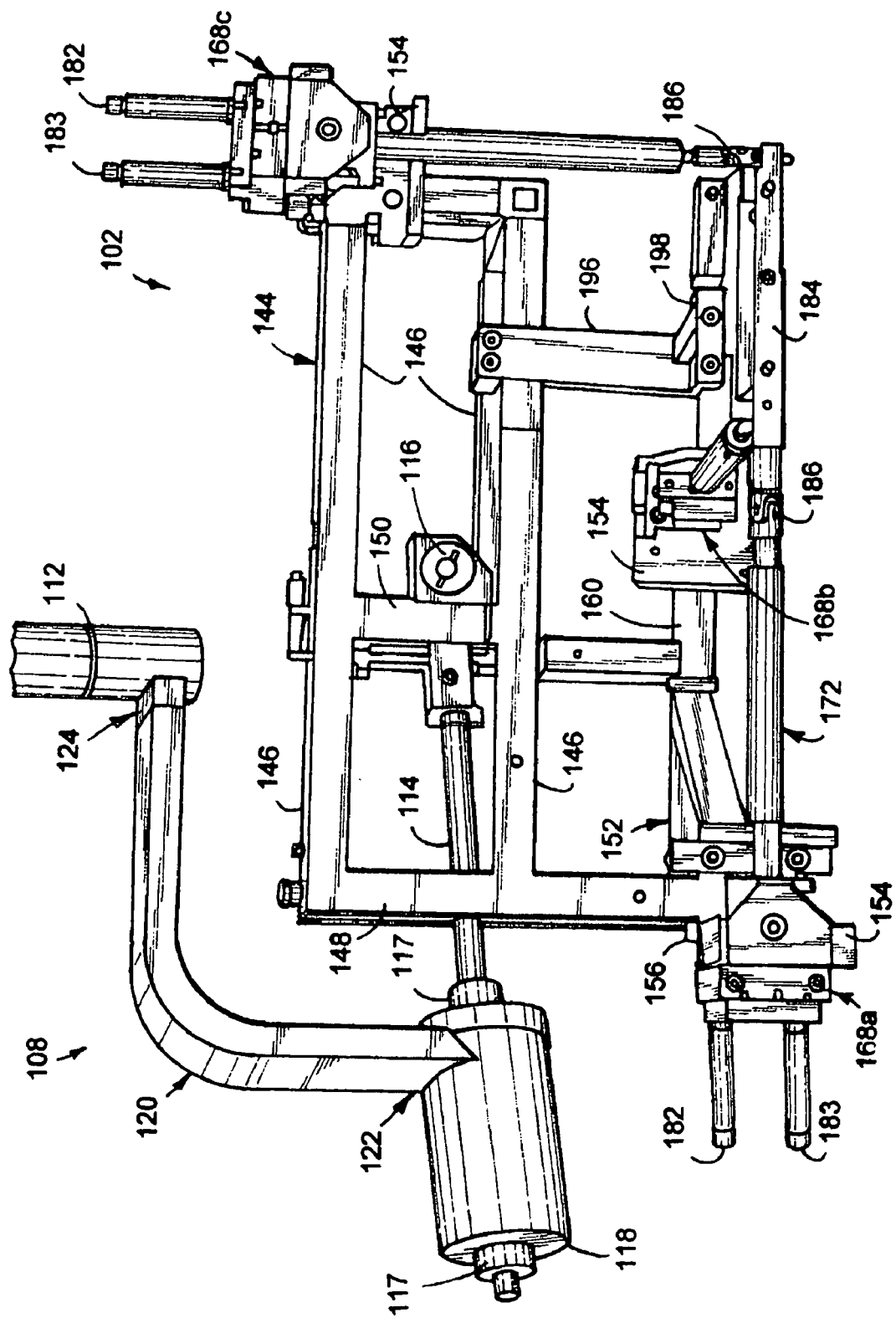
FIG. 3 is a perspective view of the recording device of the present invention with protective shields removed.

Referring back FIG. 3, the first sensor assembly 168a is positioned on the frame such that the linear translational joint is positioned substantially along an x-axis. The second sensor assembly 168b is positioned on the frame such that the linear translational joint is positioned substantially along a y-axis. The third sensor assembly 168c is positioned on the frame such that the linear translational joint is positioned substantially along a z-axis. Each sensor assembly 168a, 168b, 168c provides coordinate information along three axes relative to its respective axis positioning. The coordinate information relates to a point A[I] at the end of the translational joint where I=X, Y or Z on a three-dimensional coordinate plane. The sensor assembly also includes a fourth degree of rotational freedom of the tube 180 about the rod 178. However, this fourth degree of freedom does not influence the A[I] information of the interface and is used as an passive degree of freedom. To avoid any additional load on the jaw of the patient during the recording process, it is preferable that each sensor assembly 168a, 168b, 168c is capable of being positioned with low friction and low resistance.

Figure 5:
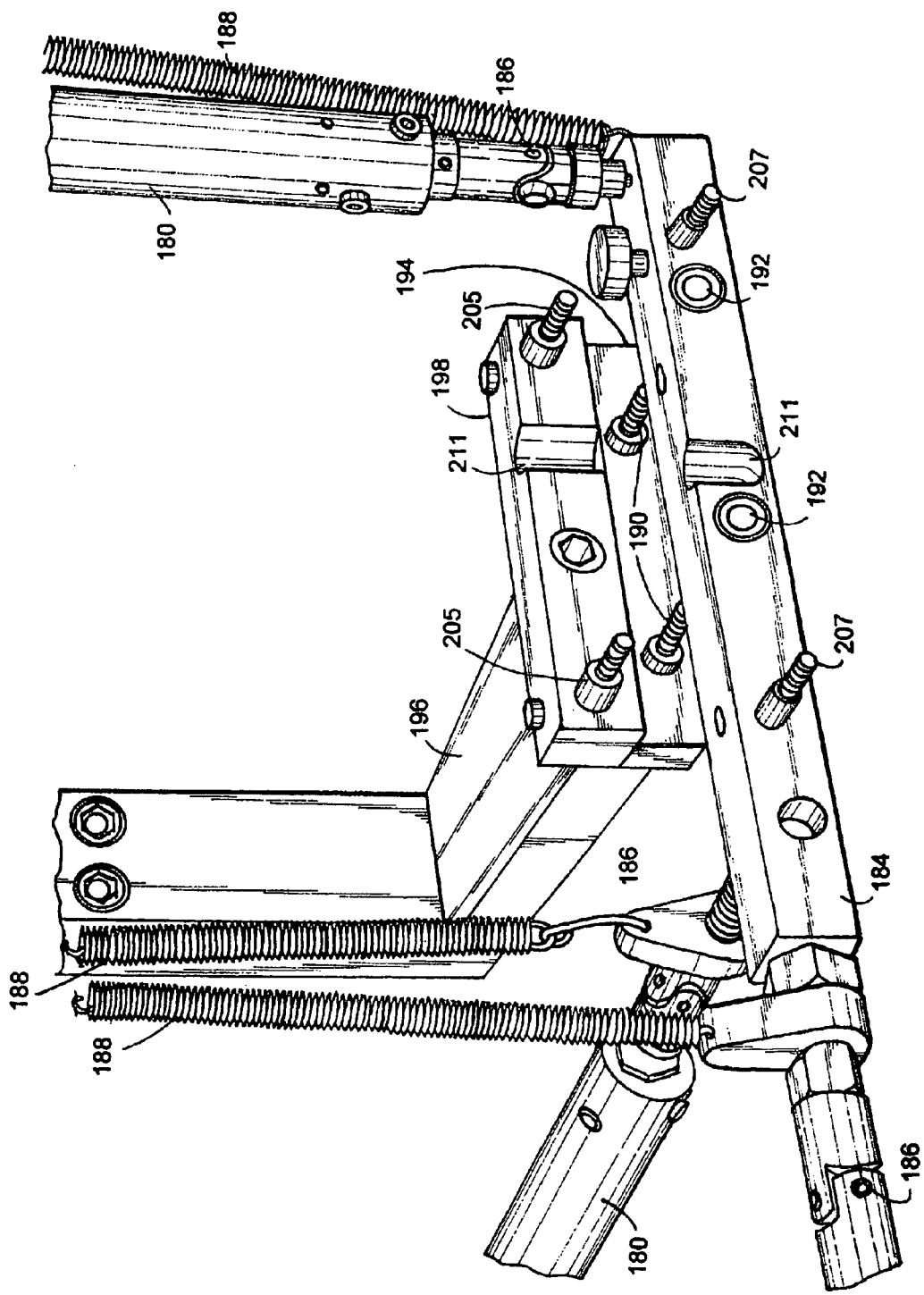
FIG. 5 is a perspective view of the recording device of the present invention illustrating a recording bar decoupled from a locking bar.
Figure 6:
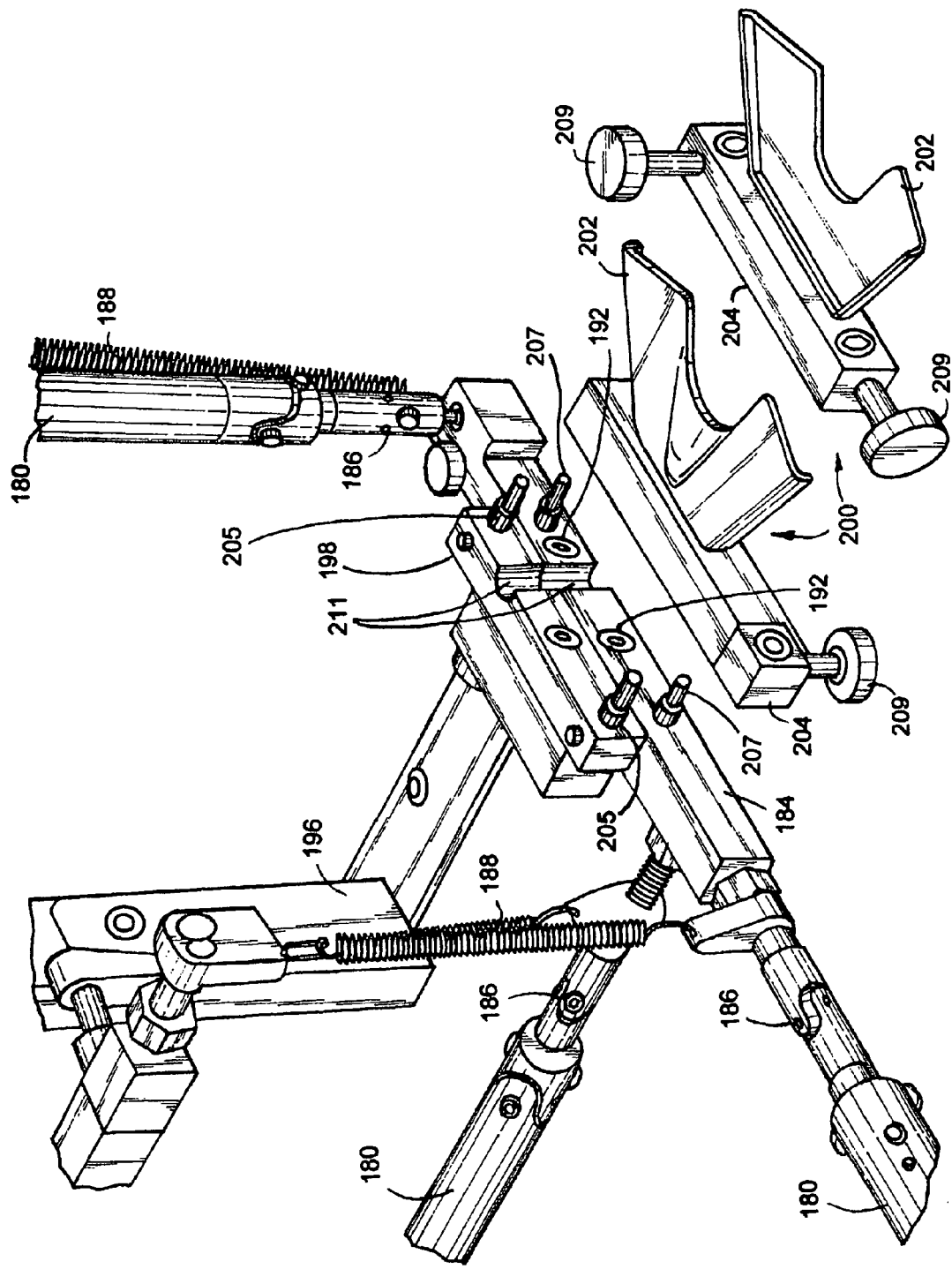
FIG. 6 is a perspective view of the recording device and clutch assemblies of the present invention illustrating the recording bar coupled to the locking bar.
Figure 7:
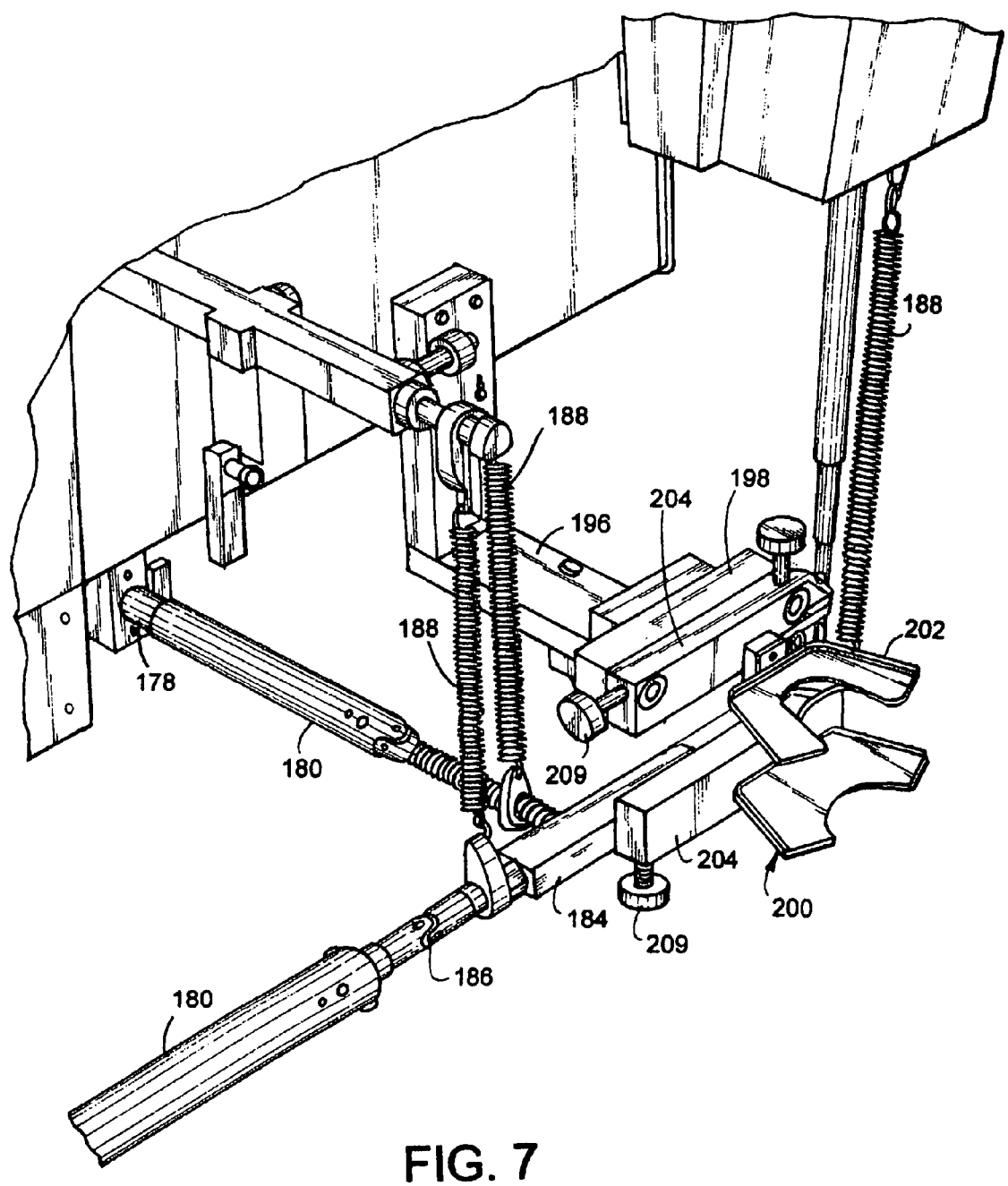
FIG. 7 is a perspective view of the recording device of the present invention illustrating the recording bar decoupled from the locking bar.

As illustrated in FIGS. 5 through 7, each sensor assembly 168a, 168b, 168c connects to an interface point on a positionable recording bar 184 by means of a universal joint 186. The recording bar 184 is suspended by springs 188 connected to the frame 144, which also provide balance to the recording bar 184 to offset the weight of the bar 184 and allow for free movement thereof when connected to the lower jaw of the patient. When not in use, or to calculate a home position, the recording bar 184 is fixedly secured to the frame 144 by connecting pins 190 insertable into mateable apertures 192 contained within the recording bar 184. The connecting pins 190 are positioned on a locking bar 194 which fixedly connects to the frame 144 via a post 196. Also fixedly attached to the post 196 is an upper bar 198 for holding the upper jaw or maxilla of the patient in a fixed position relative to the recording device 102.

The recording bar 184 is essential to the recording system because the lower jaw or mandible of the patient attaches to the recording bar 184 through a clutch device 200. The clutch device 200, which is securable to either the upper jaw or lower jaw, includes a metal, plastic or ceramic tray 202 similarly shaped to the contour of the jaws. The tray 202 is attachable to a transfer bar 204. The transfer bar 204 is in turn attachable to the respective upper bar 198, or the recording bar 184, aligned by connecting pins, 205 and 207 respectively. Each transfer bar is then frictionally secured to the respective bar 198 or 184 by threaded screws 209. Proper positioning is further ensured by detents (not shown) positioned on each transfer bar 204 mateable with indents 211 contained with the upper bar 198 and the recording bar 184. Using a clutch device 200 for each jaw, the lower jaw of the patient is securable to the recording bar 184, and the upper jaw of the patient is securable to the upper bar 198. It should be noted, though, that when the jaws of the patient are connected to the recording device 102, the recording device 102 itself is still permitted to move in three-dimensional space as it is suspended by the revolute arm 110 and wrist 108. Thus, the patient is still permitted to slightly move their head or body during the recording process without interfering with the recording itself. This provides an extra degree of comfort to the patient who does not have to support the recording device, as was typically required in the prior art, and further allows the patient to move their head and jaws in a natural state during the entire recording process.

To monitor the movement of the jaw, the initial location and orientation of the recording bar 184 must be recorded to obtain the real time position of each jaw. The recording bar 184 connects to each sensor assembly 168a, 168b, 168c through the universal joint 186 with interface point A[I] at the center of each universal joint 186. The universal joint 186 provides two angular degrees of freedom between each respective sensor assembly 168a, 168b, 168c and the respective attachment point on the bar. A third degree of freedom, in the form of the rotation of the tube 180 about the sensor rod 178, is a passive degree of freedom and is not recorded.

To sustain a repeatable and accurate recording in real time, the computer utilizes a system of high speed data acquisition channels 206 to condition, read-in and store the information simultaneously from each sensor assembly. Such hardware is made commercially available through National Instruments of Austin, Tex. Two digital I/O channels are used to allow the dentist to control the process of recording in hands-free mode through two foot operated switches. A first switch 208 signals the computer when to initiate the software while a second switch 210 starts and stops the recording.

The recording system 100 of the present invention represents a combination of multiple degrees of freedom in a mechanical system to acquire positional information of mandibular movement as collected by the sensor assemblies 168a, 168b, 168c and stored within a data storage medium controlled and included within the computer 106. The positional information from the sensor assemblies 168a, 168b, 168c, however, is not used directly for mandibular or tempormandibular joint motion analysis, but must first be converted into an output file, such as trajectory information of the tempormandibular joint's condyles, or motion of the lower jaw, before it can be understood and interpreted by the practicing dentist. To achieve this, a set of coordinate systems mathematically connects to and associates with key parts of the recorder 102. It is also important to establish all major sets of parameters called domains for each coordinate system. Such domains include TMJ domain, Sensor Domain, Joint Domain and Lower Jaw Domain.

The TMJ Domain is associated with coordinates of each center of the condyles and the rotational angle about the axis through each condyle. It can be represented as a set of three-dimensional coordinates, namely Left(X,Y,Z) for the left condyle, Right(X,Y,Z) for the right condyle, and an angle A. In reality, however, there are only six independent parameters, instead of seven, because the distance from the left condyle right condyle stays relatively constant.

The Sensor Domain includes the nine sensors contained within the three sensor assemblies. The Sensor Domain is considered to be a nine degrees of freedom domain. There is a cross-coupling relationship between these nine parameters to provide only six independent degrees of freedom information for the position of the recording bar 184.

Joint Domain represents all mechanical joints used by the recorder device 102 as a part of the multiple degrees of freedom linkage. Represented by Kinematic Mode or Displacement Mode.

Lower Jaw Domain, also referred to as World Domain, reflects the six degrees of freedom of the lower jaw measured relative to the reference or home coordinate system. Lower Jaw Domain, with its coordinate system rigidly associated with the recording bar 184, or lower transfer bar 204 which is just a simple offset away from the recording bar 184, has six parameters, or six degrees of freedom, with three translational degrees of freedom, X, Y and Z off the center of the recording bar, and three rotational degrees of freedom, consisting of pitch, yaw and roll.

When attached to the lower jaw of the patient, the lower clutch 200 and recording bar 184 move in World Domain, but each sensor assembly detects positioning of the recording bar 184 in Sensor Domain. These readings, referred to as feedbacks, are sent to the computer system 106 for processing. The processing in this case means converting information from Sensor Domain into the Lower Jaw Domain. This transformation is required to establish a kinematic model of the entire system using coordinate systems associated with each individual element of the system. It should be noted that there are two major kinematic transformations, namely Direct Kinematic Transformation ("DKT") and Inverse Kinematic Transformation ("IKT"). Both transformations convert known information in one domain into information for another domain. The Direct Kinematic Transformation is performed when the A(I) parameters of the patient's jaw are known or given. This transformation would convert it into sensor domain information. The Inverse Kinematic Transformation is used when the information from all nine sensors is obtained in the form of feedback information from each sensor, and the position of the jaws in World Domain shall be obtained. DKT is always unique and relatively fast. IKT is constrained to the Sensor Domain. However, if the number of degrees of freedom in Sensor Domain is greater than six, a damped least square method is used to determine the optimal solution for the World Domain. Thus the use of over constrained and redundant sensor systems increases the accuracy and repeatability of the conversion process going from Sensor Domain into World Domain. Use of direct and inverse Jacobian matrices allows both transformations to be performed at very high sampling rates in real time application such as recording by the software application.

Prior to beginning the recording process, the clutch 200 is secured to the upper jaw and the lower jaws of the patient before each being attached to the recorder device 102. As is known in the art, the tray 202 of each clutch 200 is fillable with a compound material and formed in the patient's mouth in a centered relation position. The clutches are then temporarily cemented to the teeth. The trays 202, when positioned inside the mouth of the patient contact through the lower pin and the upper dome surface and keep the teeth of the upper and lower jaw apart and work as an interface between the recording device 102 and jaws of the patient. The clutches 200 also permit exclusive recording of the tempormandibular joint movements without interference from the teeth. While this type of clutch pairing is similar to manual pantograph recording processes known in the art, it should be noted that practicing of the present invention is not meant to be limited to any particular type of clutch, and any other type of suitable clutch is well within the scope of the present invention.

The recording process can be started after both jaws of the patient are secured to the respective clutch system 200, with the upper clutch being secured to the upper bar 198 of the recording device 102, and the lower clutch being secured to the recording bar 184. At this reference or home position, the recording bar 184 is locked in place by the docking pins 190 positioned on the locking bar 194 just below the upper bar 198. Recording can begin at this home position to determine the home coordinates. Thereafter, the recording bar 184 is released from the docking pins 190 and the mandible becomes free of any unnatural constraints to be moved relative to the maxilla. There are four different movements during recording which in dentistry are defined as border movements. During border movement recording, the patient moves the jaw guided by the dentist to the border, or limit, of the envelope of function. The four border movements are the right and left lateral, protrusion and jaw hinging movements. The four aforementioned border movements are typical of a traditional recording process as currently used by dental professionals. However, the recording device of the present invention is not limited to those four motions, but can be employed for any arbitrary jaw movement within the physiological constraints of the jaw, including chewing process or any other movement within the border.

Recording the four border movements permits establishing a hinge axis. The hinge axis represents an imaginary line connected between geometric centers of the left and right condyles of the tempormandibular joint. More precisely, this line passes through those centers. As it is known in dentistry, during about the first 1 to 20 millimeters of mouth opening, the tempormandibular joint performs nearly pure rotational motion around the hinge axis which is functioning at this point as an instant hinge. Upon establishing the hinge axis, the computer system utilizes a software program to determine the location of the aforementioned center points in the Lower Jaw Domain coordinate system. This is accomplished by determining in the first 1 to 20 mm of mouthing opening the least variation in the condyles. From the rotation about this point, which is assumed to be pure rotational movement, an ideal arc can be extrapolated, upon which can be determined the position of the hinge axis C, and horizontal H and vertical V values for use in setting up an alignment device 224 to properly position dental casts 214 of the patient, as will be discussed. Now on those points C, H and V, their coordinates become a part of the transfer bar coordinate system and are moved within this coordinate system during any other moves of the lower jaw. During the border movements to determine right and left lateral movement, the recording device obtains and sends the raw information to the data acquisition channels 206, which the computer 106 stores in the data storage medium 212 the trajectory of both central points of the left condyle and the right condyle, as well as the angle of rotation of the jaw about the hinge axis. The last movement is called protrusive motion wherein the jaw is moved forward and is recorded in much the same manner. Results are stored in the data storage medium 212 in the form of multi-degree of freedom time history files. Any cross section of this multi-degree of freedom data structure represents all information about the position and orientation of the lower jaw with its condyle center points in three-dimensional space. The results thereof can be presented in traditional form as recognized by one skilled in the art as a series of two-dimensional graphs using Frontal, Horizontal and Sagital projections. Alternatively, the results can be represented in three-dimensional space using either a mechanical articulator 300 or within a virtual environment. Preferably, the mechanical articulator for use with the present invention is that as described in concurrently filed U.S. application Ser. No. 12/105,249 entitled APPARATUS AND METHOD FOR REPLICATING MANDIBULAR MOVEMENT, the entirety of which is incorporated herein by reference.

Figure 8:
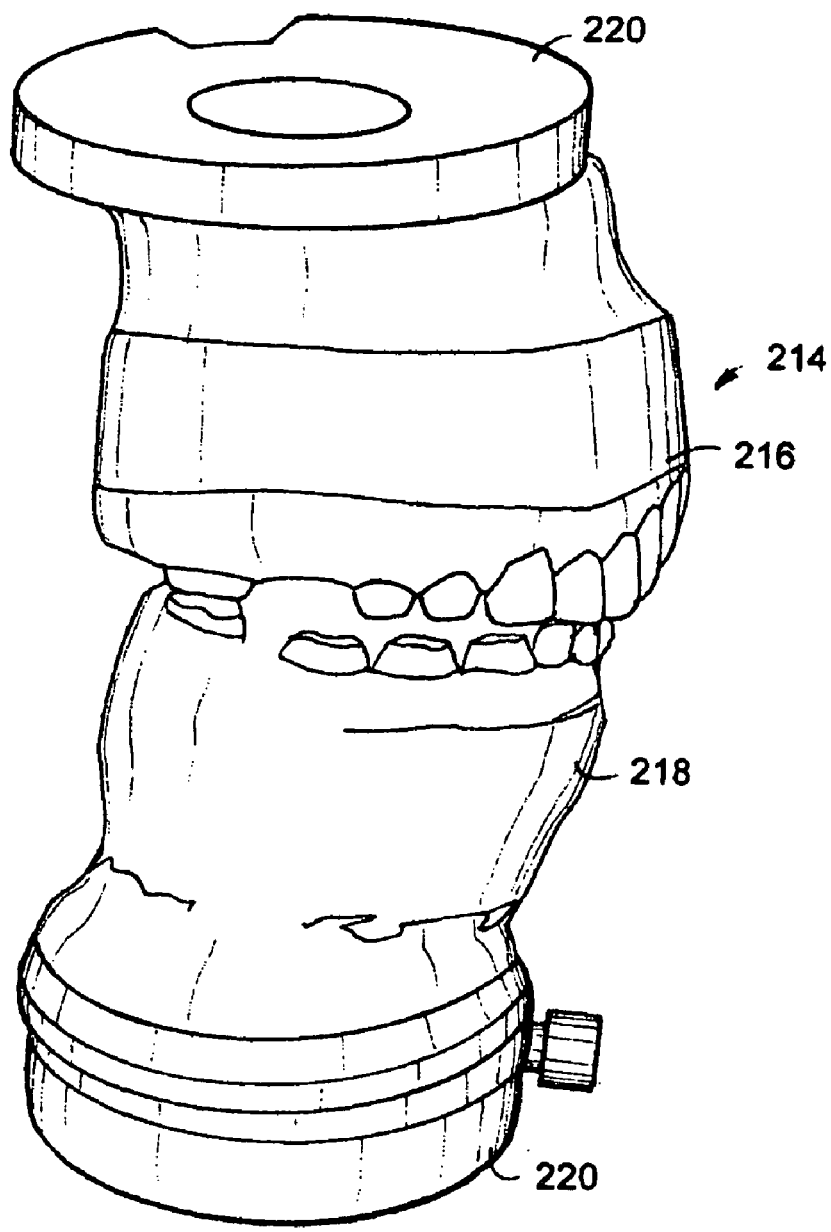
FIG. 8 is a perspective view of dental casts of the upper and lower jaw for use with the present invention.

Upon recording and obtaining the positional data of the patient's mandibular movement, the dental casts 214 of the patient's upper and lower jaw are made to more accurately analyze the occlusal relations in either the virtual or mechanical format. FIG. 8 illustrates an upper dental cast 216 positioned in relation to a lower dental cast 218, each mounted to a magnetic base 220. Each magnetic base 220 is mateable with a corresponding receiving base 222 positioned on the articular 224. It should be noted, though, that some analysis can be done during or immediately after the recording process by the computing means 106 and the user interface 104 by using a generic dental cast previously scanned and stored within the computer. However, for the most accurate analysis, dental casts of the actual patient are preferred.

While the making of dental casts 214 has long been known and practiced within the art, the present invention provides a unique method of making the dental casts such that their spatial relationship with one another is preserved throughout the entire recording and replicating process, whether such replication be done either a virtual environment or mechanically. Further, it should be noted that the casting of the patient's upper and lower jaw can be done prior to recording. If done prior to recording, virtual representation of the mandibular movement is viewable in real-time on the user interface during the recording process.

Figure 9:
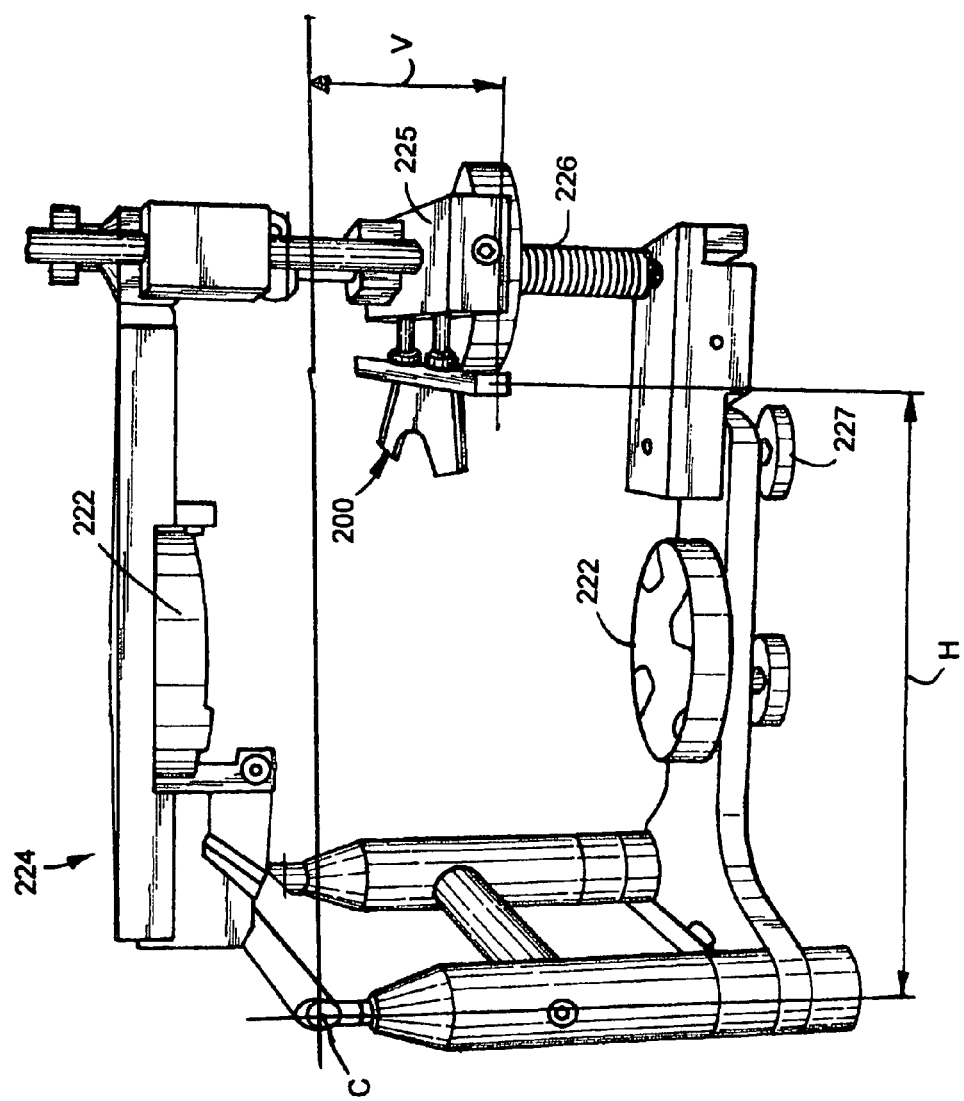
FIG. 9 is a perspective view of an alignment device for forming the dental casts of FIG. 8 in accordance with the present invention.

To begin, the tempormandibular joint parameters are obtained during the recording process and used by the software program to determine a set of corresponding parameters H and V to establish proper mounting conditions of the dental cast of the lower jaw on a alignment device used to form the dental casts in static occlusal. As illustrated in FIG. 9, the set of parameters include vertical V and horizontal H settings, and are measured from point C representing the hinge axis of the left and right condyles in the Lower Jaw Domain coordinate system. The user reads these values off the user interface 104 and adjusts the alignment device to correspond thereto. To create a support, the lower jaw is positioned into the same location relative to the tempormandibular joint hinge C obtained during the recording. The alignment device 224 has two degrees of freedom to manipulate the location of the lower cast, corresponding to the H and V parameters. Adjusting the alignment device 224 includes attaching a clutch 220 to a mounting bracket 225. The mounting bracket rests upon a threaded bolt 226 and is vertically adjustable by rotating the bolt to obtain the proper V value. Adjust for the H value, the two halves of the alignment device are moved relative to one another by loosening set screw 227. The upper dental cast 216 and the lower dental cast 218 are then formed in much the same fashion as is known in the art by filling the gaps between the dental cast and the respective magnetic base with plaster. At this position, the adjustable alignment device 224 allows the lower cast 218 to pivot around the true hinge axis C determined by the tempormandibular joint during recording. It should be noted that the previously described method of forming the dental casts is not limited to any one type of alignment device 224, and modifications to its structure while still accomplishing the same result is well within the scope of the present invention.

Figure 10:
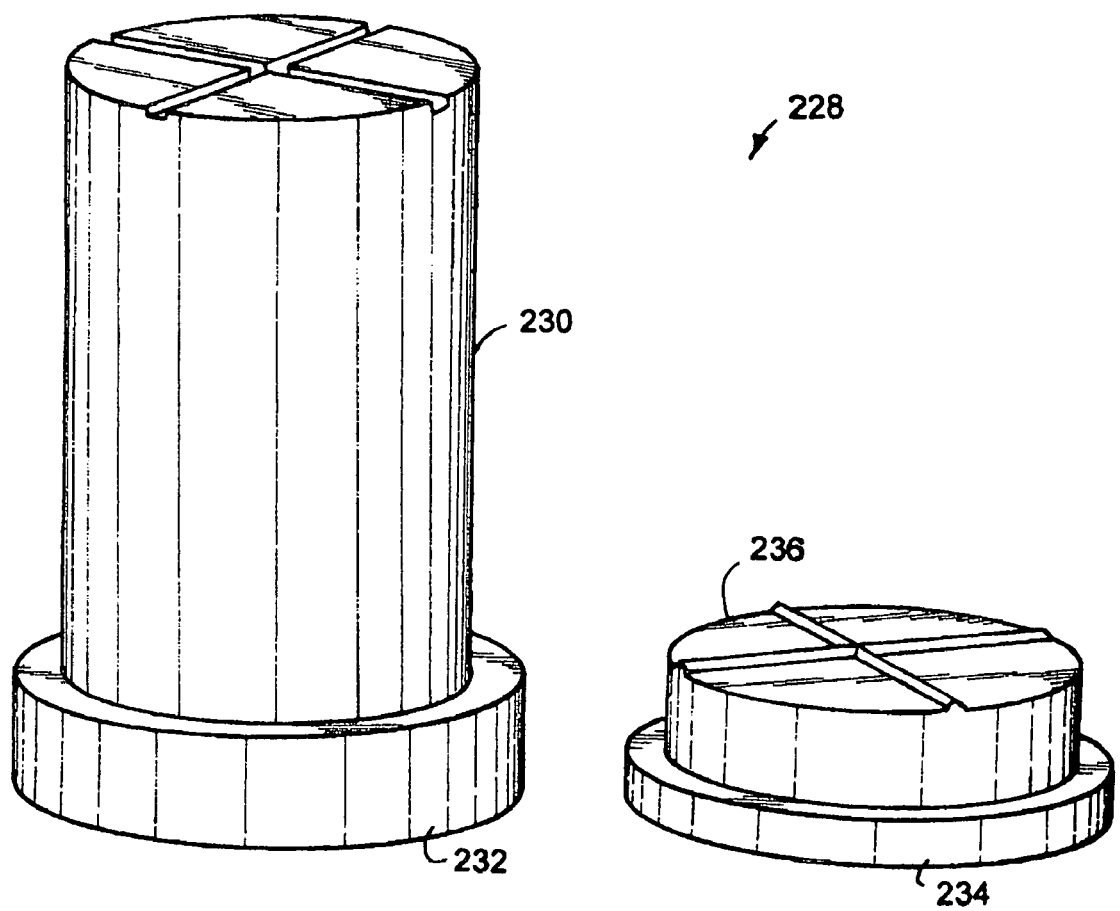
FIG. 10 is a perspective view of a calibrating bar for use in accordance with the present invention.
Figure 11:
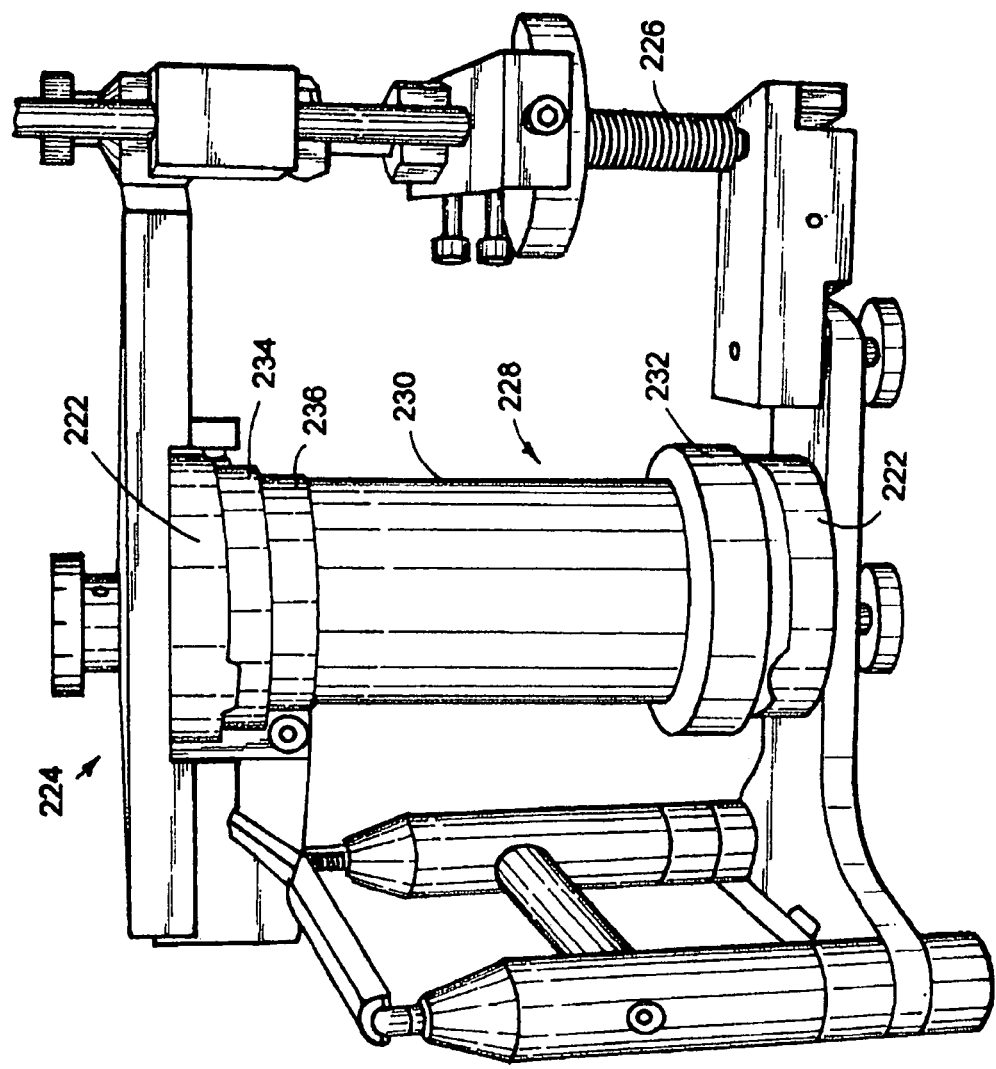
FIG. 11 is a perspective view of an alignment device having the calibrating bar FIG. 10 disposed therein in accordance with the present invention.

After making the casts, a calibrating bar 228 is used to determine a home or initial reference position of the alignment device 224. As illustrated in FIG. 10, the calibrating bar 228 includes a cylinder 230 connected to a magnetic base 232, and another magnetic base 234. As illustrated in FIG. 11, the calibrating bar 228 is fitted within the alignment device 224 an plaster 236 is filled in the space between the cylinder 230 and the magnetic base 234. Each base 232, 234 is mateable with bases 222 of the articulator such that rotation motion is not permitted. Alternatively, the calibrating bar can be adjusted prior to making the dental casts, as all that is needed to do either is a knowledge of the H and V values. Regardless of when the calibration takes place, this procedure is done only once to calibrate the fixture.

Figure 12:
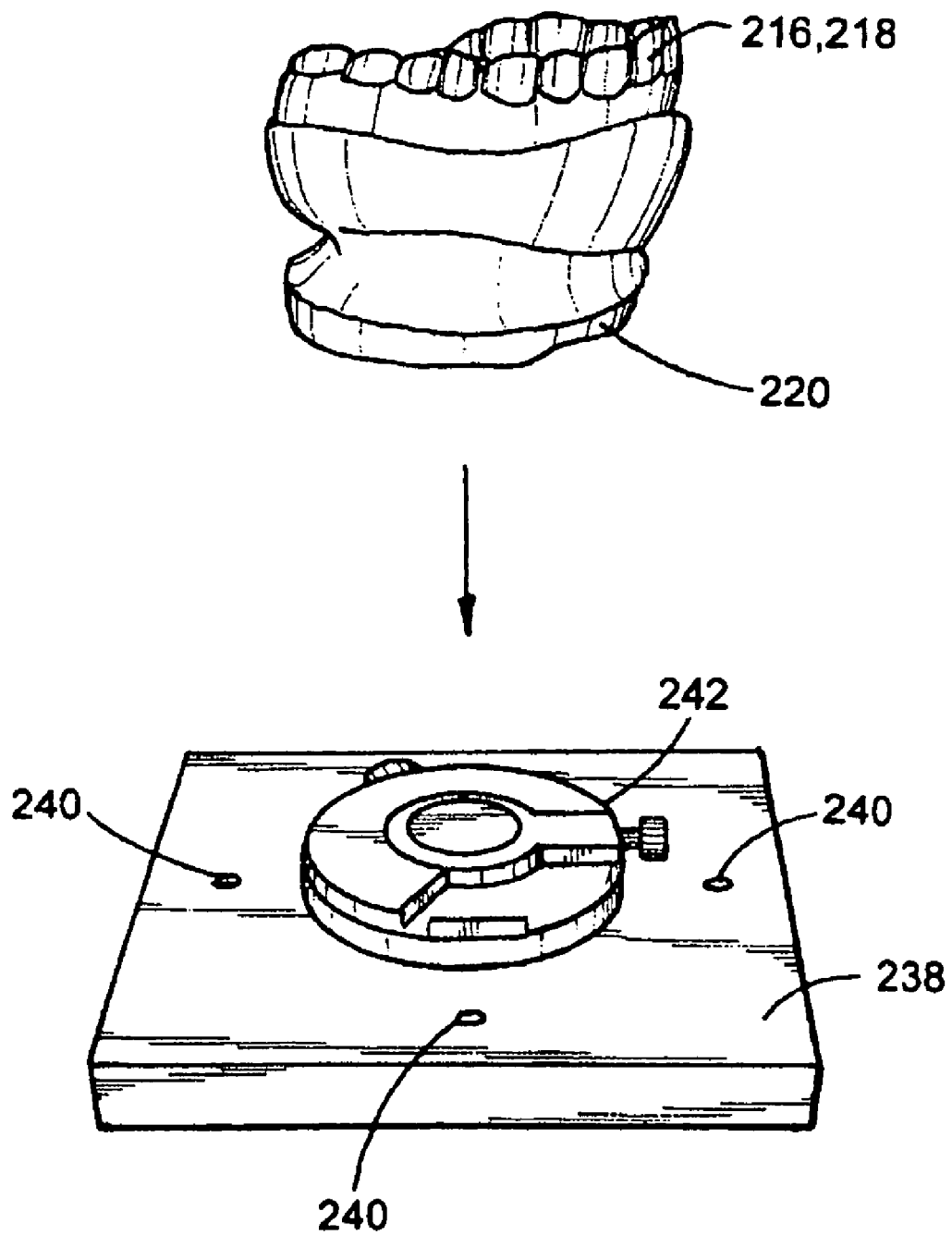
FIG. 12 is a perspective view of a fixture and dental cast for use in accordance with the present invention.

The calibration bar 228 is used to homogenize positioning 238 fixtures for scanning each dental cast and applying the casts to a mechanical articulator. By employing the aforementioned steps, the correct relationship between the two casts is preserved at a given home or initial reference position during scanning, mechanical articulation, or virtual modeling. Once the H and V values are known for a specific patient, they do not need to be recalculated, nor do any of the instruments need to be recalibrated upon using the calibrated calibration bar 228. This has been found to be quiet advantageous, especially in regards to replicating movement in the virtual environment. For example, as illustrated in FIG. 12, a dental cast is secured to a fixture 228. The fixture contains a magnetic base 240, along with apertures 242 for securing the fixture during the scanning process. Because the H and V values are known for either the upper dental cast or the lower dental cast, a three dimensional scan of either cast can be later used by a computer software program having the proper occlusion and mandibular movement about a known hinge axis C. The prior art was unable to do this because there was no technique available to preserve both the occlusal relationship between each jaw and tempormandibular joint movement.

To view the results using three-dimensional space in the virtual environment, the dental casts 216, 218 must first be digitally scanned. To achieve high precision images and at the same time preserve the integrity of the data, each dental cast 216, 218 is mounted to a fixture 238 to hold the cast 216, 218 at a fixed position during scanning, as is illustrated in FIG. 12. Preferably, the scanners primarily include a device capable of surface scanning with high resolution and being able to format or convert the information from the scanning device into a data file. Each dental cast 216, 218 is then scanned or digitized, and this information transferred to the data storage medium 212, operated by the computer 106, in the form of three-dimensional meshes. At this point, a matrix of coordinate transformations is determined which is used later on during the virtual modeling for proper handling of the position of parts on the screen. Scanning of each dental cast individually on the fixture maintains the integrity and association between both jaws in its reference coordinate system, enabling a digital representation and proper storage of the scanned data for future display and analysis.

To demonstrate movement of the lower jaw relative to the upper jaw in a virtual environment, a set of animation software is used. Preferably, the software tool for the development of the three-dimensional package is one as developed by the inventors of the present invention. Said software was developed using a DirectX® package developed by Microsoft® and widely used by other developers in the field of three-dimensional animation, including CAD/CAM packages. A program called PolyTrans, as distributed by Okino Computer Graphics of Mississauga, Ontario, Canada, was used to convert the scanned data from the industry standard .STL format into an .X format which is supported by DirectX®. Implementation of the entire virtual articulator package in DirectX® for three-dimensional motion of the scanned surfaces was done in a Visual Basic environment.

The software program can simulate practically any motion of the temporomandibular joint on the screen of the user interface 104.

When using the program as developed by the present inventors, the positional data obtained during the recording process can be used to synthesize or replicate motion of the tempormandibular joint. Further, either software package can interface the virtual environment with the recording device, so virtual representation of the mandibular movement can be viewed in real time throughout the recording process.

Virtual mandibular motion can be controlled by a mouse as well as by a joystick, or the like. Virtual mandibular motion allows the user to change not only the position on the user interface screen of the upper and lower jaws, or portions thereof, but also the location of the light source and view point. An unguided, non-border chewing movement can also be recorded and observed on the virtual articulator. Also, the user can virtually rotate the jaws in all directions to observe the movements in different views The user may also turn the entire image and work it from different perspectives, which indicates the base moving together with the lower jaw as an option. Alternatively, the product may display both jaws as well.

The last segment of the virtual environment includes a 'fly-through' capability. As a part of the virtual world package, this feature allows the dentist to control with a joy stick, similar to a pilot in a small airplane, and fly through all the parts and components on the screen and observe all the specific parts of the jaw in minute detail. This is extremely useful in the virtual diagnosis and redesigning of new teeth as use of three-dimensional displays makes an enormous difference in understanding the problem.

Alternatively, scanning of the jaws or the tempormandibular joint is done with high resolution computed tomography (CT) technology, so the density of both the bones and the tissues can be determined. This has been termed volumetric scanning versus surface scanning that obtains only the mesh for the models using surface scanners. The information is stored in standard Digital Imaging and Communications in Medicine (DICOM) format. Just as .STL is standard for surface scans, the DICOM is standard for any CT scan machine, whatever the application may be. As a result, the scan shows the density of bones for a pair of jaws which is very important information for the dental restoration process. For implant dentistry, it is critical to know the character and density of the bone. If bone material is insufficient, a graft will be placed to increase the size and density. The next step would be to superimpose these images of the casts (outside mesh only) with image of the CT scan. This image would be a shell around the volumetric area and besides moving them together the doctor can always click a particular location and see the density of the bones around this area, whether the patient has a sufficient support for the bridge, crown or an implant. That information may be taken in form of the three-dimensional volumetric image from the NewTom type of machine and can be incorporated with a surface image, and then be displayed and moved on the screen based on any desired trajectory.

The virtual environment package of the present invention uses the same drive files obtained from the recorder to display the movement of a jaw in three-dimensional space. The virtual mandibular movement can be used for analysis of tooth geometry as well as TMJ kinematics. The virtual environment package also allows user to move/adjust the jaw in any of six degrees of freedom. The virtual environment package was developed by using the aforementioned DirectX technology and can be considered as a "plug and play" option for Dental CAD packages. This virtual articulator of the present invention has an interface to a joystick so the user can control the position of the jaw not only with the computer mouse but with a three-dimensional joystick as well. This capability is critical for the virtual articulation when it is extended by a few more features such as the fly-through option.

Although the present invention has been described with reference to preferred embodiments, workers skilled in the art will recognize that changes may be made in form and detail without departing from the spirit and scope of the invention.

The invention claimed is:

1. An apparatus for use in dentistry to obtain positional data related to movement about a maxilla, the apparatus comprising:
   a support frame;
   a maxilla member attached to the support frame, the maxilla member to secure the maxilla of the patient in a fixed position;
   a plurality of electro-mechanical sensor assemblies attached to the support frame, each electro-mechanical sensor assembly including a base fixedly attachable to the support frame, a first gimbal pivotally attached to the base, a second gimbal pivotally attached orthogonally to the first gimbal, a first elongated member attached to the second gimbal, and a second elongated member slidably engageable with the first elongated member; and
   a mandibular member connected to the second elongated member of each electro-mechanical sensor assembly, the mandibular member positionable proximate the maxilla member, the mandible of the patient securable to the mandibular member, wherein each electro-mechanical sensor detects movement of the mandibular member with three degrees of freedom.

2. The apparatus of claim 1 wherein each electro-mechanical sensor assembly further comprises:
   a first sensor to obtain data relative to movement of the first gimbal;
   a second sensor to obtain data relative to movement of the second gimbal; and
   a third sensor to obtain data relative to translational movement of the second elongated member about the first elongated member.

3. The apparatus of claim 1 wherein each electro-mechanical sensor assembly further comprises:
   a first sensor to detect positioning of the first gimbal;
   a second sensor to detect movement of the second gimbal; and
   a third sensor to detect positioning of the first elongated member relative to the second elongated member.

4. The apparatus of claim 1 wherein the first electro-mechanical sensor assembly obtains positional data proximately along an x-axis, wherein the second electro-mechanical sensor assembly obtains positional data proximately along a y-axis, and wherein the third electro-mechanical sensor assembly obtains positional data proximately along a z-axis.

5. The apparatus of claim 4 wherein the positional data each sensor assembly obtains along each axis includes pitch, yaw and translational positioning of the mandibular member.

6. The apparatus of claim 1 and further comprising a locking mechanism connected to the support frame to lock the mandibular member in a home position wherein the mandibular member is immovable relative to the maxilla member.

7. The apparatus of claim 1 and further comprising a spring connected to the support frame and the mandibular member, wherein the spring dampens movement of the mandibular member.

8. The apparatus of claim 1 wherein three electro-mechanical sensor assemblies are employed, whereby nine sensors obtain the patient's occlusal data to establish over constrained movement of the patient's mandible with using nine degrees of freedom.

9. An apparatus for use in dentistry to obtain positional data related to movement of a mandible about a maxilla, the apparatus comprising:
- a support frame;
- a maxilla support member fixedly attached to the support frame;
- a mandibular member positionable proximate the maxilla member;
- a first sensing assembly attached to the support frame and connected to the mandibular member, the first sensing assembly to obtain a first set of positional data of the mandibular member proximately along a x-axis;
- a second sensing assembly attached to the support frame and connected to the mandibular member, the second sensing assembly to obtain a second set of positional data of the mandibular member proximately along a y-axis; and
- a third sensing assembly attached to the support frame and connected to the mandibular member, the third sensing assembly to obtain a third set of positional data of the mandibular member proximately along a z-axis wherein each sensing assembly comprises:
  - a base member attached to the support frame;
  - a first gimbal member pivotally secured to the base member;
  - a second gimbal member pivotally secured to the first gimbal member, the second gimbal member pivotal orthogonal to the first gimbal member;
  - a first elongated member attached to the second gimbal member; and
  - a second elongated member slidably engageable with the first elongated member, the second elongated member connected to the mandibular member.

10. The apparatus of claim 9 wherein each set of positional data includes data related to pitch, yaw and translational positioning of the mandibular member proximately along the respective axis.

11. The apparatus of claim 9 wherein each sensing assembly further comprises:
- a first sensor to obtain data relative to movement of the first gimbal member;
- a second sensor to obtain data relative to movement of the second gimbal member; and
- a third sensor to obtain data on the movement of the first elongated member relative to the second elongated member.

12. The apparatus of claim 9 wherein each sensing assembly further comprises:
- a first sensor to detect pivotal positioning of the first gimbal member;
- a second sensor to detect pivotal positioning of the second gimbal member; and
- a third sensor to detect translational positioning of the first elongated member relative to the second elongated member.

13. The apparatus of claim 9 wherein the positional data each sensor assembly obtains includes pitch, yaw and translational positioning of the mandibular member proximately along the respective axis.

14. The apparatus of claim 9 wherein the support frame is suspended by a support mechanism independent of the patient.

15. An apparatus for use in dentistry to obtain occlusal data of a patient, the patient having a maxilla and a mandible, the apparatus comprising:
- a support frame;
- a stationary maxilla member attached to the support frame, the maxilla of the patient securable to the maxilla member;
- a moveable mandibular member positioned in cooperable relation to the maxilla member, the mandible of the patient securable to the mandibular member;
- a first sensing assembly attached to the support frame and connected to the mandibular member, the first sensing assembly for obtaining data relative to pitch, yaw and translational movements of the mandibular member about a x-axis;
- a second sensing assembly attached to the support frame and connected to the mandibular member, the second sensing assembly for obtaining data relative to pitch, yaw and translational movements of the mandibular member about a y-axis; and
- a third sensing assembly attached to the support frame and connected to the mandibular member, the third sensing assembly for obtaining data relative to pitch, yaw and translational movements of the mandibular member about a z-axis, wherein the data obtained by the sensing assemblies provide an over constrained sensing system with nine degrees of freedom wherein each sensing assembly comprises:
  - a base member attached to the support frame;
  - a first gimbal member pivotally secured to the base member;
  - a second gimbal member pivotally secured to the first gimbal member, the second gimbal member pivotal orthogonal to the first gimbal member;
  - a first elongated member attached to the second gimbal member; and
  - a second elongated member slidably engageable with the first elongated member, the second elongated member connected to the mandibular member.

16. The apparatus of claim 15 wherein each sensing assembly further comprises:
- a first sensor to obtain data relative to pivotal movement of the first gimbal member;
- a second sensor to obtain data relative to pivotal movement of the second gimbal member; and
- a third sensor to obtain data relative to translational movement of the first elongated member relative to the second elongated member.

17. The apparatus of claim of claim 15 and further comprising a support mechanism to suspend the support frame independent of the patient.

* * * * *